(12) United States Patent
Chia et al.

(10) Patent No.: US 10,667,863 B2
(45) Date of Patent: Jun. 2, 2020

(54) SURGICAL LASER TREATMENT TEMPERATURE MONITORING

(71) Applicant: Boston Scientific Scimed, Inc., Maple Grove, MN (US)

(72) Inventors: Wen-Jui Ray Chia, Sunnyvale, CA (US); Thomas C. Hasenberg, Campbell, CA (US); Hui Wang, Fremont, CA (US); Brian Christopher Carlson, Minnetrista, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 915 days.

(21) Appl. No.: 15/031,107

(22) PCT Filed: Oct. 20, 2014

(86) PCT No.: PCT/US2014/061319
§ 371 (c)(1),
(2) Date: Apr. 21, 2016

(87) PCT Pub. No.: WO2015/061201
PCT Pub. Date: Apr. 30, 2015

(65) Prior Publication Data
US 2016/0262834 A1  Sep. 15, 2016

Related U.S. Application Data

(60) Provisional application No. 61/934,387, filed on Jan. 31, 2014, provisional application No. 61/895,211, filed on Oct. 24, 2013.

(51) Int. Cl.
*A61B 18/00* (2006.01)
*A61B 18/22* (2006.01)
*A61B 18/20* (2006.01)

(52) U.S. Cl.
CPC .... *A61B 18/22* (2013.01); *A61B 2018/00589* (2013.01); *A61B 2018/00607* (2013.01);
(Continued)

(58) Field of Classification Search
CPC .......... A61B 18/22; A61B 2018/00589; A61B 2018/00607; A61B 2018/00625;
(Continued)

(56) References Cited

U.S. PATENT DOCUMENTS 5,104,392 A  4/1992  Kittrell et al.
7,869,016 B2  1/2011  Mitchell et al.
(Continued)

FOREIGN PATENT DOCUMENTS

CN  1261774 A  8/2000
JP  S 61-257638 A  11/1986
(Continued)

OTHER PUBLICATIONS

International Search Report for PCT/US2014/061319, dated Jan. 20, 2015 (4 pages).
(Continued)

*Primary Examiner* — Michael W Kahelin
*Assistant Examiner* — Vynn V Huh
(74) *Attorney, Agent, or Firm* — Bookoff McAndrews, PLLC

(57) ABSTRACT

A surgical laser system includes a laser source configured to generate laser energy, a laser fiber optically coupled to the laser source and configured to discharge the laser energy and collect electromagnetic energy feedback from a treatment site a photodetector configured to generate an output signal in response to the electromagnetic energy collected from the treatment site, a display, and a controller configured to
(Continued)

produce an image or indication about the temperature at the treatment site on the display based on the output signal.

16 Claims, 8 Drawing Sheets

(52) U.S. Cl.
CPC .............. *A61B 2018/00625* (2013.01); *A61B 2018/00642* (2013.01); *A61B 2018/00672* (2013.01); *A61B 2018/00678* (2013.01); *A61B 2018/00791* (2013.01); *A61B 2018/00809* (2013.01); *A61B 2018/20361* (2017.05)

(58) Field of Classification Search
CPC ........... A61B 2018/00642; A61B 2018/00672; A61B 2018/00678; A61B 2018/00791; A61B 2018/00809
See application file for complete search history.

(56) References Cited

U.S. PATENT DOCUMENTS

| | | | |
|---|---|---|---|
| 2004/0006339 A1* | 1/2004 | Underwood | ....... A61B 18/1402 606/45 |
| 2004/0162490 A1 | 8/2004 | Soltz et al. | |
| 2005/0251116 A1 | 11/2005 | Steinke et al. | |
| 2009/0149845 A1 | 6/2009 | Brown | |
| 2015/0230864 A1* | 8/2015 | Xuan | ..................... A61B 18/22 606/2.5 |

FOREIGN PATENT DOCUMENTS

| | | | | |
|---|---|---|---|---|
| JP | H 01-250271 A | 10/1989 | | |
| JP | H 02-279169 A | 11/1990 | | |
| JP | 2001-503645 A | 3/2001 | | |
| JP | 2005-502389 A | 1/2005 | | |
| JP | 2005-185829 A | 7/2005 | | |
| JP | 2008-543505 A | 12/2008 | | |
| JP | 2012-40106 A | 8/2012 | | |
| JP | 2012-519554 A | 8/2012 | | |
| JP | 2013-516245 A | 5/2013 | | |
| WO | WO 2010/102246 A1 | 9/2010 | | |
| WO | WO 2010102246 A1 * | 9/2010 | ............. | A61B 18/22 |
| WO | WO 2012/071388 A2 | 5/2012 | | |

OTHER PUBLICATIONS

International Preliminary Report on Patentability for corresponding International Application No. PCT/US2014/061319, dated Apr. 26, 2016 (8 pages).

* cited by examiner

SURGICAL LASER TREATMENT TEMPERATURE MONITORING

CROSS-REFERENCE TO RELATED APPLICATIONS

This application is a U.S. national stage entry under 35 U.S.C. § 371 of International PCT Application No. PCT/US2014/061319, filed on Oct. 20, 2014, which claims the benefit of U.S. Provisional Application No. 61/895,211, filed Oct. 24, 2013, and U.S. Provisional Application No. 61/934,387, filed Jan. 31, 2014. The content of each of the above-referenced applications is incorporated herein by reference in its entirety for all purposes.

FIELD OF THE INVENTION

Embodiments of the present invention relate generally to the field of medical lasers utilizing optical fibers. More specifically, embodiments of the present invention relate to the use of electromagnetic energy feedback from a treatment site to provide a physician with real-time information about conditions at the treatment site, such as, for example, tissue temperature, laser treatment being performed, etc.

BACKGROUND

Embodiments of the present invention generally relate to surgical laser systems and methods of operating or controlling such systems.

Surgical laser systems have been used in various practice areas, such as, for example, urology, neurology, otorhinolaryngology, general anesthetic ophthalmology, dentistry, gastroenterology, cardiology, gynecology, and thoracic and orthopedic procedures. Generally, these procedures require precisely controlled delivery of laser energy as part of the treatment protocol to cut, vaporize or ablate targeted tissue, such as cancerous cells and prostate tissue, for example.

Black body radiation is one of the basic phenomena in physics, which has been commonly used for measuring the temperature of the body. Generally, the subject in thermodynamic equilibrium will radiate electromagnetic waves having a specific spectrum and intensity that depends only on the temperature of the body.

U.S. Pat. No. 7,869,016, which is assigned to the same assignee as the present application and the contents of which are incorporated herein by reference in their entirety for all purposes, discloses a technique for protecting the laser fiber tip by monitoring the black body radiation from the fiber tip. The intensity of the black body radiation is used to indicate a temperature of the fiber tip, which is used to automatically shut off the discharge of the laser energy when the temperature reaches an unsafe condition. Thus, in this instance, a physician does not have the ability to alter the laser procedure being formed or to change the operating parameters of the laser device to avoid system shut down.

The temperature achieved by exposing tissue or a treatment site to laser energy plays an important role in determining the type of laser treatment being performed (e.g. coagulation, vaporization, etc.), as well as the effectiveness of the laser treatment. For example, it may not be possible to perform a vaporization treatment or the vaporization treatment may be inefficient, if the temperature is too low at the treatment site. Additionally, the temperature sensed at the treatment site may also indicate that the laser fiber, from which the laser energy is discharged, may suffer damage due to overheating the fiber tip.

It would be desirable to provide real-time laser treatment site temperature information to assist the physician during a surgical laser treatment to: identify the laser treatment being performed, improve the efficiency of the laser treatment by, for example, preventing overtreatment or under treatment, warn the surgeon of potential fiber tip damage, and/or provide other benefits currently unavailable to physicians.

SUMMARY

Embodiments of the present invention are directed to a surgical laser system including laser source configured to generate laser energy and a laser fiber optically coupled to the laser source and configured to discharge the laser energy and collect electromagnetic energy feedback from a treatment site in a patient. The surgical laser system also includes a photodetector configured to generate an output signal in response to the electromagnetic energy collected from the treatment site, a display and a controller configured to produce an image or indication about at least one condition at the treatment on the display based on the output signal.

Embodiments of the present invention are also directed to a method of operating a surgical laser system comprising the steps of generating laser energy using a laser source and discharging the laser energy through a laser fiber to a treatment site. The method also includes delivering electromagnetic energy feedback from the treatment site produced in response to discharging the laser energy to the treatment site to a photodetector and generating a photodetector output signal based on the electromagnetic energy feedback. After the photodetector output signal is generated, the photodetector output signal is analyzed using a controller to determine the treatment site information (i.e., conditions at the treatment site). Once analyzed by the controller, this treatment site information is displayed on a display for a physician to see.

In another embodiment of the present invention, a method of operating a surgical laser system is provided. The method comprises the steps of generating laser energy using a laser source, discharging the laser energy through a laser fiber to a treatment site, analyzing electromagnetic energy feedback from the treatment site produced in response to discharging the laser energy to the treatment site, and automatically adjusting the laser energy based on the analysis of the electromagnetic energy feedback.

For a better understanding of the embodiments of the present invention, its operating advantages and specific objects attained by its uses, reference is made to the accompanying descriptive matter in which preferred embodiments of the invention are illustrated in the accompanying drawings.

DETAILED DESCRIPTION OF ILLUSTRATIVE EMBODIMENTS

Figure 1:
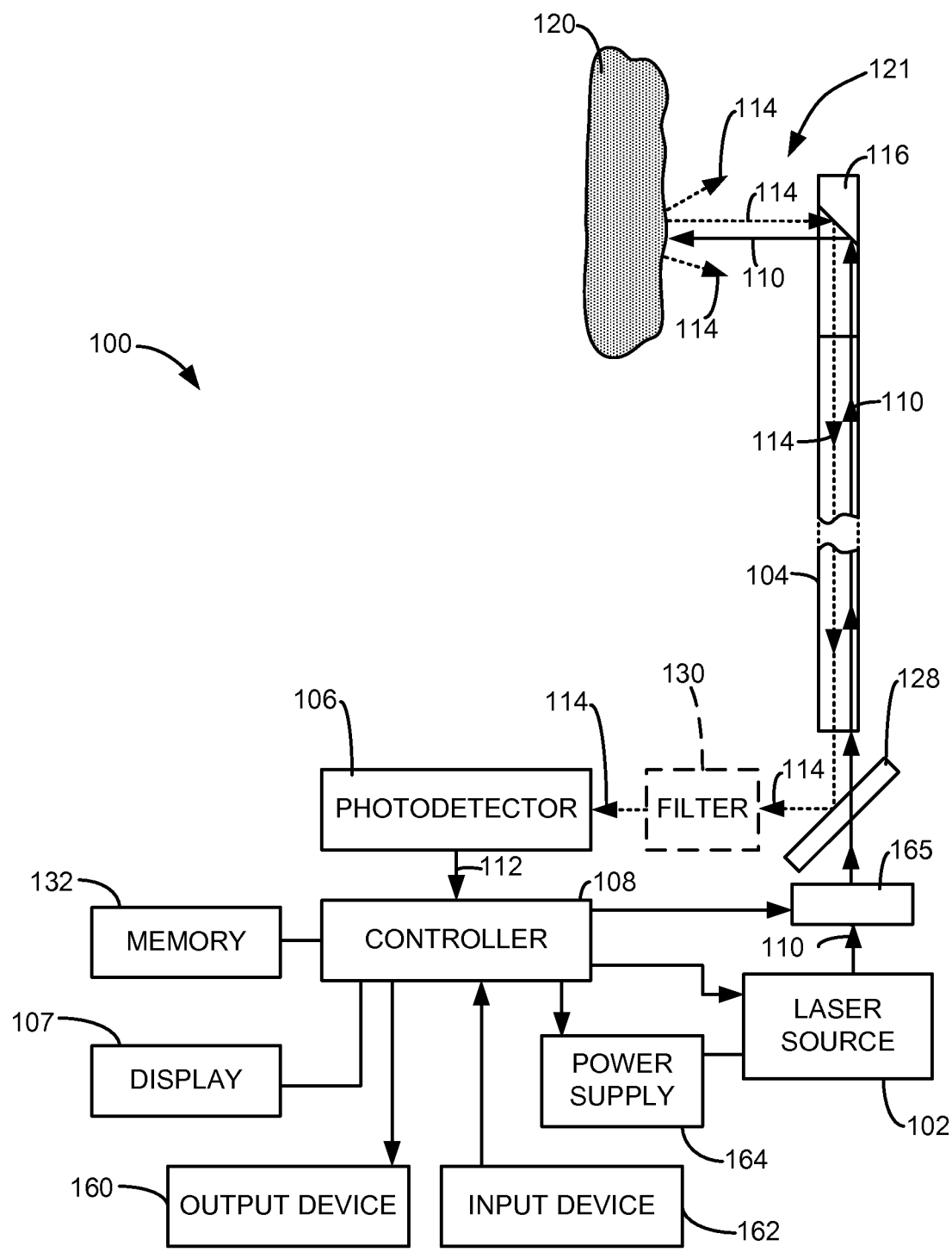
FIG. 1 is a simplified diagram of a surgical laser system in accordance with embodiments of the present invention performing an exemplary surgical laser treatment.

Embodiments of the present invention generally relate to surgical laser systems and methods of controlling surgical laser systems, such as during performance of a laser treatment on a patient. Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, the present invention may be embodied as methods, systems, and/or computer program products. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code embodied in the medium. Any suitable computer readable medium may be utilized including hard disks, CD-ROMs, optical storage devices, or magnetic storage devices.

The computer-usable or computer-readable medium referred to herein as "memory" may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present invention are also described using flowchart illustrations and block diagrams. It will be understood that each block (of the flowcharts and block diagrams), and combinations of blocks, can be implemented by computer program instructions. These program instructions may be provided to one or more controllers each comprising one or more processor circuits, such as a microprocessor, microcontroller or other processor, such that the instructions which execute on the processor(s) create means for implementing the functions specified in the block or blocks. The computer program instructions may be executed by the processor(s) to cause a series of operational steps to be performed by the processor(s) to produce a computer implemented process such that the instructions which execute on the processor(s) provide steps for implementing the functions specified in the block or blocks.

Accordingly, the blocks support combinations of means for performing the specified functions, combinations of steps for performing the specified functions and program instruction means for performing the specified functions. It will also be understood that each block, and combinations of blocks, can be implemented by special purpose hardware-based systems which perform the specified functions or steps, or combinations of special purpose hardware and computer instructions.

Embodiments of the present invention are directed to a surgical laser system and methods of operating or controlling the system to perform, for example, a surgical laser treatment on a patient, such as, coagulation, tissue vaporization, tissue ablation, tissue cutting, kidney or bladder stone fragmentation (i.e., laser lithotripsy), or other surgical laser treatments. In some embodiments, the system utilizes laser energy feedback or radiation feedback from the treatment site that is produced in response to exposure of the treatment site to laser energy generated by the system to determine an approximate temperature of the treatment site.

In some embodiments, the approximate temperature is displayed for the physician in real-time, and/or used to determine an operating mode of the system that is indicative of the laser treatment being performed at the treatment site.

FIG. 1 is a simplified diagram of a surgical laser system 100 formed in accordance with embodiments of the present invention. In some embodiments, the system 100 includes a laser source 102, a waveguide or laser fiber 104, a photodetector 106, a display 107, and a controller 108. The laser source 102 is configured to generate laser energy, generally referred to as 110. The laser fiber 104 is optically coupled to the laser source 102 using, for example, a lens or other conventional technique. The laser fiber 104 is configured to discharge the laser energy 110 generated by the laser source 102 to a targeted treatment site 120. The photodetector 106 is configured to generate an output signal 112 representative of electromagnetic energy feedback 114 produced at the treatment site 120 in response to the discharge of the laser energy 110 from the laser fiber 104. In some embodiments, the controller 108 is configured to produce an image 140 on a display 107 based on the output signal 112.

The laser source 102 may comprise one or more laser generators, which are used to produce the laser energy 110. Each laser generator may comprise conventional components, such as a laser resonator, to produce the laser energy 110 having the desired power and wavelength. In some embodiments, the laser energy 110 has a wavelength of approximately 532 nm (green laser energy). Other wavelengths of the laser energy 110 may also be used, such as laser energy having a wavelength of approximately 400-475 nm (blue laser energy), or laser energy having a wavelength of approximately 2000-2200 nm, which is suitable for performing laser lithotripsy procedures, for example. These and other wavelengths may be used for the laser energy 110 depending on the laser treatment to be performed.

Figure 2:
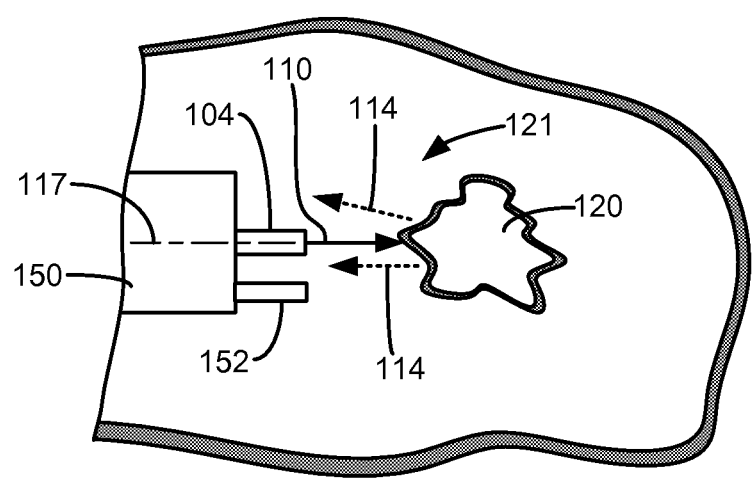
FIG. 2 is a simplified diagram of a distal end of a laser fiber of the surgical laser system of FIG. 1 within an endoscope performing an exemplary laser treatment.

In some embodiments, the laser energy 110 generated by the laser source 102 is optically coupled to the laser fiber 104 through a conventional optical coupler (not shown), which may include lenses. The laser fiber 104 may include any conventional surgical laser waveguide, such as an optical fiber. In some embodiments, the laser fiber 104 is configured to discharge the laser energy 110 at a distal end 116. The distal end or fiber tip 116 of the laser fiber 104 may be configured to discharge the laser energy 110 laterally (i.e., side-firing fiber), as shown in FIG. 1, along the axis 117 of the laser fiber 104 (i.e., end-firing fiber), as shown in FIG. 2, or in another conventional manner.

During a surgical laser treatment, the laser energy 110 is discharged from the distal end 116 of the laser fiber 104 toward targeted tissue or object 120 at the laser treatment site 121 to perform the desired laser treatment on the targeted object 120. As used herein, the term "targeted object" means an object of a patient on which a laser treatment is intended to be performed, such as a tumor, prostate tissue or other body tissue, or a kidney or bladder stone, for example. Embodiments of the invention utilize the black body radiation or electromagnetic energy feedback 114 produced at the treatment site 121 in response to the discharge of the laser energy 110 from the fiber tip 116, as an indication of the temperature at the treatment site 121 or the targeted object 120 at the treatment site, and/or as an indicator of the laser energy treatment being performed on the object 120 at the treatment site 121.

In experiments performed ex vivo on porcine kidneys, laser energy 110 was delivered to targeted tissue 120 on the porcine kidneys by a fiber 104. The black body radiation or electromagnetic energy feedback 114 produced at the treatment site 121 in response to the discharge of this laser energy 110 from the fiber tip 116 was then collected by the laser fiber 104 and analyzed. Three experiments were performed where the laser fiber 104 was moved across the targeted tissue 120 at different speeds and the resulting black body radiation or electromagnetic energy feedback 114 produced was collected and plotted on a graph.

Figure 3A:
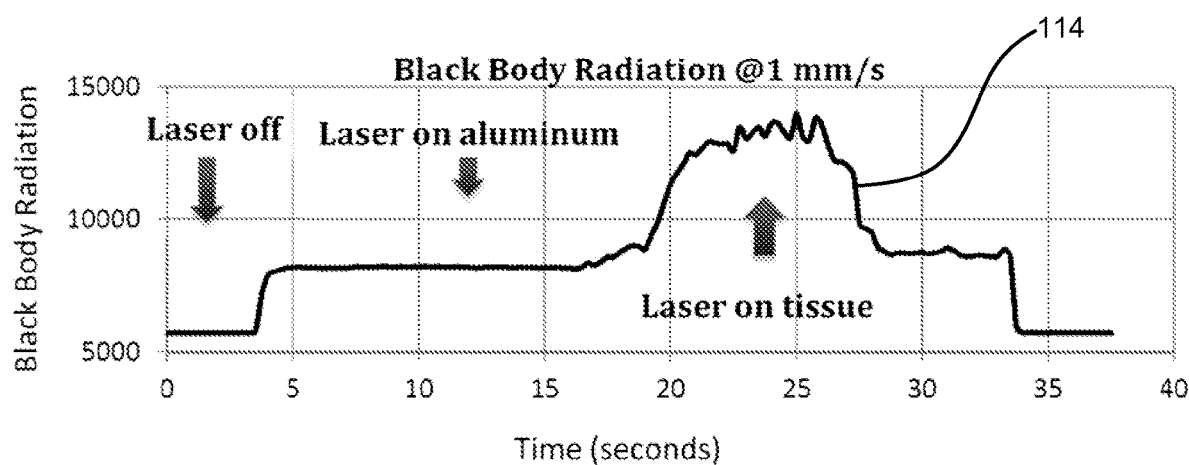
FIG. 3A is a graph depicting black body radiation as a laser fiber is moved across targeted tissue at 1 mm/s.
Figure 3B:
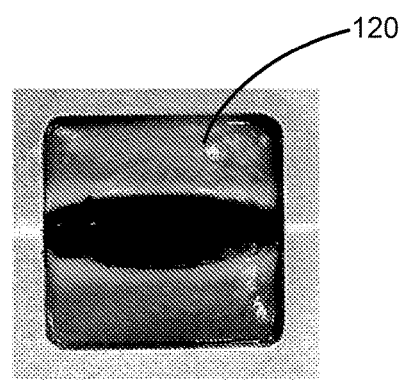
FIG. 3B is a photograph of the vaporization effect on the targeted tissue as the laser fiber is moved across the targeted tissue at 1 mm/s.

FIG. 3A is a graph that depicts the black body radiation along the Y-axis and the corresponding time in seconds along the X-axis as the laser fiber 104 was moved across the targeted tissue 120 at 1 mm/s. From 0 seconds to approximately 4 seconds, the laser source 102 was off. From approximately 4 seconds to approximately 17 seconds, the laser source 102 was turned on and the laser fiber 104 was moving across an aluminum tray that was supporting the porcine kidney. From approximately 17 seconds to approximately 28 seconds, the laser source 102 was on and the laser fiber 104 was moving across the targeted tissue 120. From approximately 28 seconds to approximately 34 seconds, the laser source 102 was on and the laser fiber 104 was moving across the aluminum tray that was supporting the porcine kidney. Lastly, at approximately 34 seconds, the laser source 102 was turned off. As can clearly be seen from the graph, the black body radiation increased from approximately 7500 to approximately 15000 when the laser fiber 104 was moving across the targeted tissue 120 between 17 seconds and 28 seconds. FIG. 3B is a photo that shows the vaporization groove created in the porcine kidney tissue 120 when the laser fiber 104 was moved across the targeted tissue 120 at a rate of 1 mm/s.

Figure 4A:
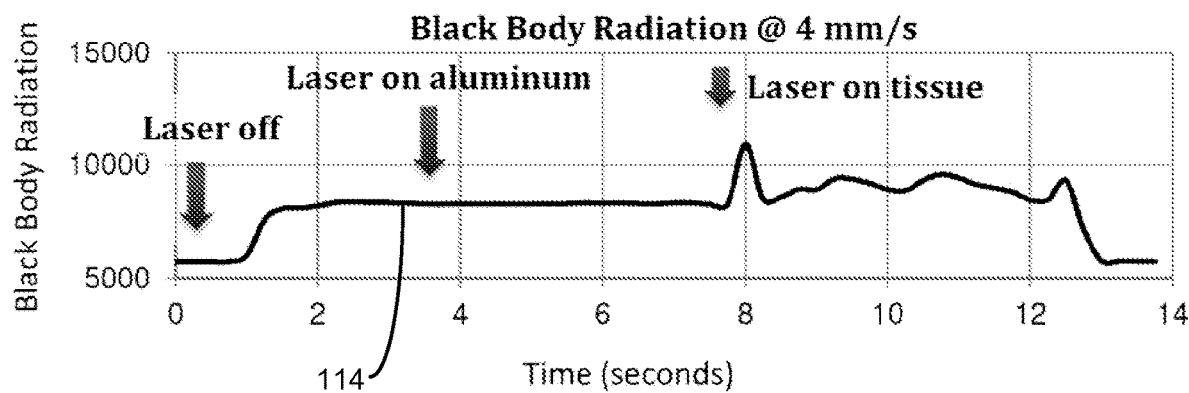
FIG. 4A is a graph depicting black body radiation as a laser fiber is moved across targeted tissue at 4 mm/s.
Figure 4B:
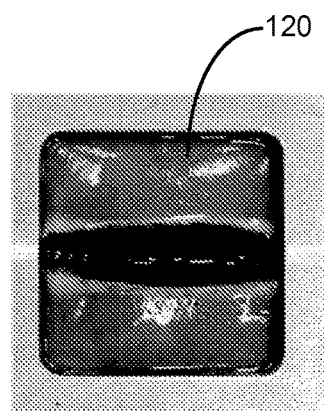
FIG. 4B is a photograph of the vaporization effect on the targeted tissue as the laser fiber is moved across the targeted tissue at 4 mm/s.

FIG. 4A is a graph that depicts the black body radiation along the Y-axis and the corresponding time in seconds along the X-axis as the laser fiber 104 was moved across the targeted tissue 120 at 4 mm/s. From 0 seconds to approximately 1 second, the laser source 102 was off. From approximately 1 second to approximately 7 seconds, the laser source 102 was turned on and the laser fiber 104 was moving across the aluminum tray that was supporting the porcine kidney. From approximately 7 seconds to approximately 13 seconds, the laser source 102 was on and the laser fiber 104 was moving across the targeted tissue 120. At approximately 13 seconds, the laser source 102 was turned off. As can clearly be seen from the graph, the black body radiation increased from approximately 7500 to approximately 10000 when the laser fiber 104 was moving across the targeted tissue 120 between 7 seconds and 13 seconds. FIG. 4B is a photo that shows the vaporization groove created in the porcine kidney tissue 120 when the laser fiber 104 was moved across the targeted tissue 120 at a rate of 4 mm/s.

Figure 5A:
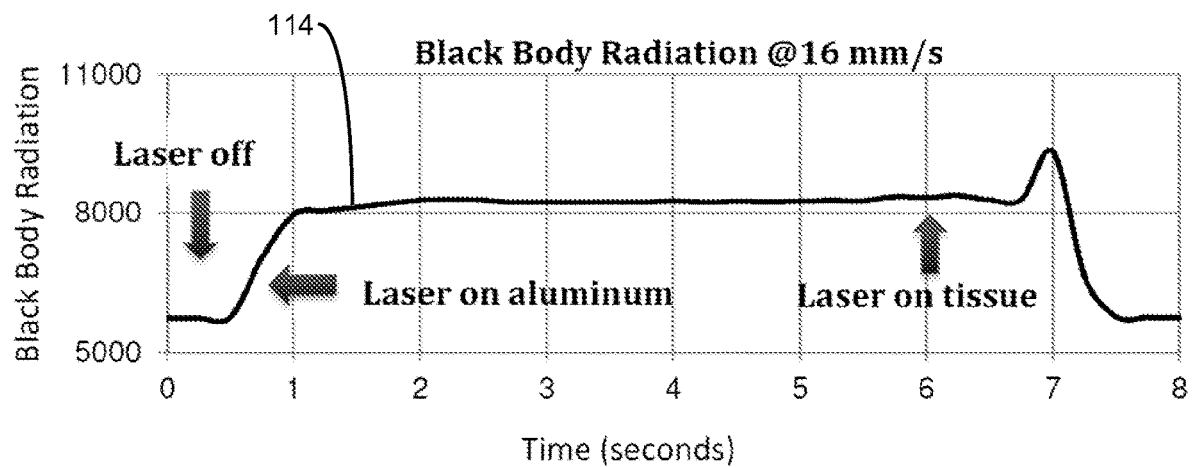
FIG. 5A is a graph depicting black body radiation as a laser fiber is moved across targeted tissue at 16 mm/s.
Figure 5B:
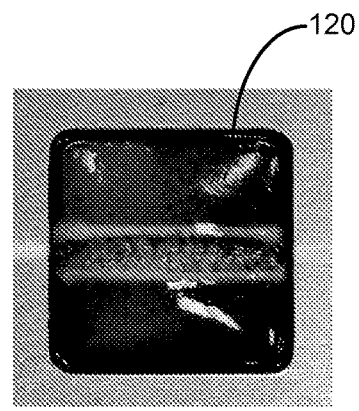
FIG. 5B is a photograph of the vaporization effect on the targeted tissue as the laser fiber is moved across the targeted tissue at 16 mm/s.

FIG. 5A is a graph that depicts the black body radiation along the Y-axis and the corresponding time in seconds along the X-axis as the laser fiber 104 was moved across the targeted tissue 120 at 16 mm/s. From 0 seconds to approximately 0.5 seconds, the laser source 102 was off. From approximately 0.5 seconds to approximately 1.5 seconds, the laser source 102 was turned on and the laser fiber 104 was moving across the aluminum tray that was supporting the porcine kidney. From approximately 1.5 seconds to approximately 7.5 seconds, the laser source 102 was on and the laser fiber 104 was moving across the targeted porcine tissue 120. At approximately 7.5 seconds, the laser source 102 was turned off. As can clearly be seen from the graph, the black body radiation increased from approximately 8000 to approximately 8500 when the laser fiber 104 was moving across the targeted tissue 120 between 1.5 seconds and 7.5 seconds. FIG. 5B is a photo that shows the vaporization groove created in the porcine kidney tissue 120 when the laser fiber 104 was moved across the targeted tissue 120 at a rate of 16 mm/s.

As depicted in FIGS. 3A, 4A and 5A, one can clearly identify an increase in the black body radiation or electromagnetic energy feedback 114 produced when the laser source 102 was on and the laser fiber 104 moved across the targeted tissue 120. Also, as depicted in FIGS. 3B, 4B and 5B, by moving the laser fiber 104 across the targeted tissue 120 at different speeds, one can create different degrees of vaporization such that vaporization increases when the laser fiber 104 is moved across the targeted tissue 120 at slower speeds (FIG. 3B) and vaporization decreases when the laser fiber 104 is moved across the targeted tissue 120 at slower speeds (FIG. 5B). Because the degree of vaporization correlates to the temperature of the targeted tissue being vaporized, one can also correlate the temperature of the targeted tissue 120 being vaporized to the black body radiation or electromagnetic energy feedback 114 produced.

Figure 6:
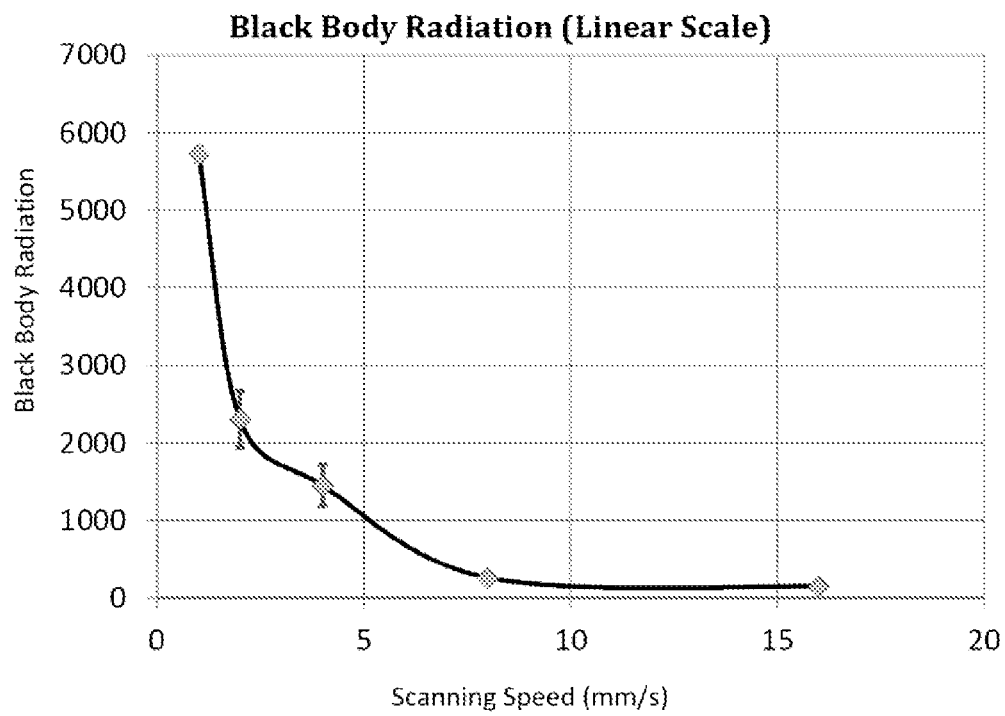
FIG. 6 is a graph in linear scale depicting the black body radiation as a function of laser fiber scanning speed.
Figure 7:
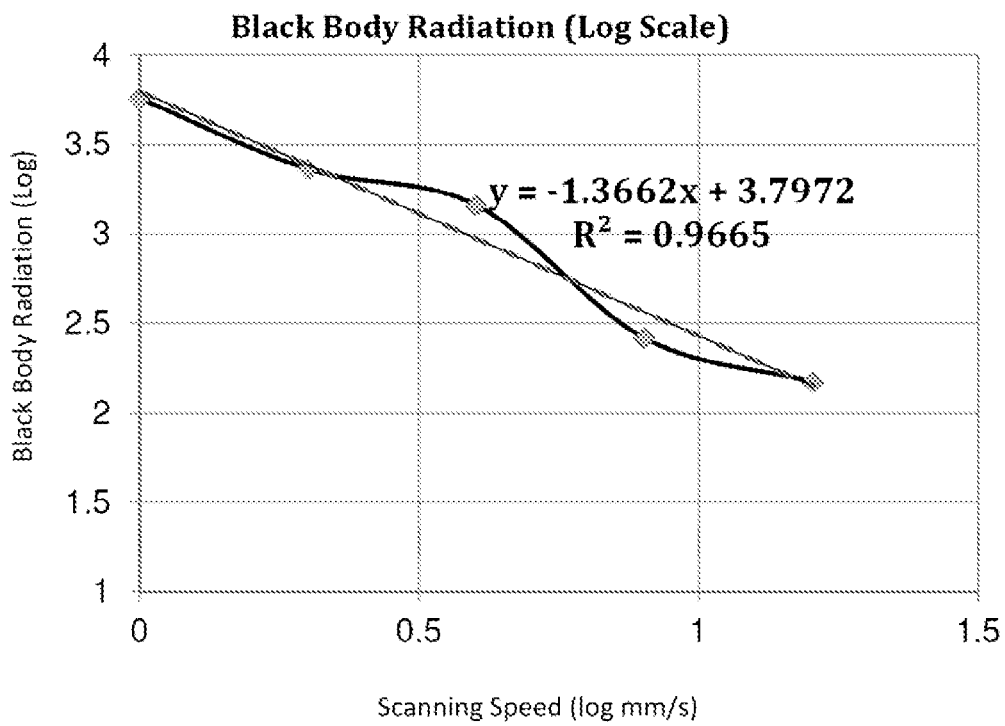
FIG. 7 is the graph depicted in FIG. 6 in logarithmic scale.

Depicted in FIGS. 6 and 7 are graphs showing the correlation of the intensity of the black body radiation 114 and hence, the vaporization degree to the laser fiber 104 scanning or moving speed across the targeted tissue 120. As can clearly be seen in FIG. 6 where the values along the X and Y axes are in linear scale, the black body radiation intensity 114 (Y axis) increases with the degree of vaporization, which corresponds to an increase in the targeted tissue 120 temperature. As can clearly be seen in FIG. 7, with the values along the X and Y axes now in logarithmic scale, there is a high correlation between vaporization degree and blackbody radiation intensity 114, where the correlation coefficient $r^2$ is close to 1. Therefore, we believe that one can use the black body radiation or electromagnetic energy feedback 114 produced on the targeted tissue 120 as an indicator of tissue vaporization degree. Accordingly, based on the electromagnetic energy feedback 114 produced on the targeted tissue 120, the current operating mode or laser treatment being performed at the treatment site (i.e., coagulation, low vaporization, high vaporization, carbonization, etc.) can be identified in real-time and communicated back to the physician instantaneously.

In some embodiments, the electromagnetic energy feedback 114 (or black body radiation) collected from the fiber tip 116 is delivered to the photodetector 106 through either the laser fiber 104 or through another component. Because the electromagnetic energy feedback 114 is light in the infrared (IR) or far infrared (FIR) range that is emitted at the treatment site 121 as temperature increases as a result of the laser treatment, this IR or FIR light is collected by the laser fiber 104 and transmitted back to the photodetector 106 as a result of the laser fiber 104 having the ability to transmit light in two directions. Once the electromagnetic energy feedback 114 is received and analyzed by the photodetector 106, the photodetector 106 produces an output signal 112 that is indicative of an approximate temperature at the treatment site 121, such as the temperature of the targeted object 120.

In some embodiments, the system 100 includes a dichroic beam splitter or a mirror 128 that reflects the electromagnetic energy feedback 114 while allowing the laser energy 110 to pass through, as shown in FIG. 1. The electromagnetic energy feedback 114 reflected by the mirror 128 is delivered to the photodetector 106. It is understood that the components of the system 100 could be modified such that the mirror 128 reflects the laser energy 110 from the laser source 102 to the optical coupler, while allowing the electromagnetic energy feedback 114 to pass through the mirror 128.

In some embodiments, the mirror 128 is highly transmissive over the wavelengths of the laser energy 110 and highly reflective over the wavelengths of the electromagnetic energy feedback 114. Thus, electromagnetic energy feedback 114, which is the black body radiation of targeted objects 120 at the treatment site 121 having a wavelength that is different from the wavelength of the laser energy 110, may be reflected by the mirror 128 to the photodetector 106 while the laser energy 110 discharged from the laser source 102 passes through the mirror to the laser fiber 104.

In some embodiments, the mirror 128 includes a central hole (not shown), through which the laser energy 110 generated by the laser source 102 is discharged. Portions of the electromagnetic energy feedback 114 impact the mirror 128 outside the edges of the hole, and are reflected by the mirror 128 to the photodetector 106. This embodiment of the mirror is particularly necessary when the electromagnetic energy feedback 114 comprises the reflected laser energy 110.

In some embodiments, the system 100 includes one or more filters 130 that are configured to filter frequencies of the electromagnetic energy feedback 114, and deliver filtered electromagnetic energy feedback 114 to the photodetector 106. Exemplary embodiments of the one or more filters 130 include a low-pass filter, a high-pass filter, and/or a band-pass filter. For example, a band-pass filter between 1.4 um to 1.8 um can be used to monitor the electromagnetic feedback 114, although even longer wavelength band-pass filters can also be useful. Thus, embodiments of the output signal 112 include an output signal 112 generated by the photodetector 106 in response to the electromagnetic energy feedback 114 or the filtered electromagnetic energy feedback 114. In order to simplify the discussion, references to the output signal 112 include the output signal 112 generated in response to the filtered or unfiltered electromagnetic energy 114, unless described otherwise or inapplicable.

In some embodiments, the one or more filters 130 and photodetector 106 may be replaced with a spectrometer that analyzes the electromagnetic energy feedback 114 and outputs information, such as intensity levels of the electromagnetic energy feedback 114 over a range of wavelengths or frequencies, and/or other information. In some embodiments, the spectrometer outputs only intensity levels of the electromagnetic energy feedback 114 at certain frequencies of interest. In order to simplify the discussion, references to the output signal 112 should also be interpreted as describing embodiments in which the output signal 112 is replaced with spectrometer information generated by a spectrometer in response to an analysis of electromagnetic energy feedback 114.

In some embodiments, the controller 108 represents conventional electronics and processors that may execute program instructions stored in memory 132 of the system 100, or other locations, to perform various functions described herein. In some embodiments, the controller 108 processes (e.g., amplifies) and/or analyzes the output signal 112 to determine an approximate temperature indicated by the signal 112 of the treatment site 121 and/or the targeted objects 120. In some embodiments, the system 100 is calibrated to ensure that the approximate temperature indicated by the output signal 112 is an accurate approximation of the actual temperature at the treatment site 121.

In some embodiments, the output signal 112 can be analyzed and displayed to determine the Joule usage corresponding to different vaporization levels or different laser treatments being performed.

In some embodiments, electromagnetic energy feedback 114 can be modulated using an optical chopper or any other intensity modulator or inherent modulation (such as Q-switch pulsed laser) to generate a modulated output signal 112 from the photodetector 106. The controller 108 can then demodulate this signal through a demodulator, such as phase-locked loop or multiplier using software or additional hardware included with the controller, to extract the electromagnetic energy feedback 114. In this way, the signal-to-noise ratio can be improved by eliminating any environmental or background electromagnetic energy, such as the energy of radiation from the laser cavity, and any dark noise from the photodetector 106.

Figure 8:
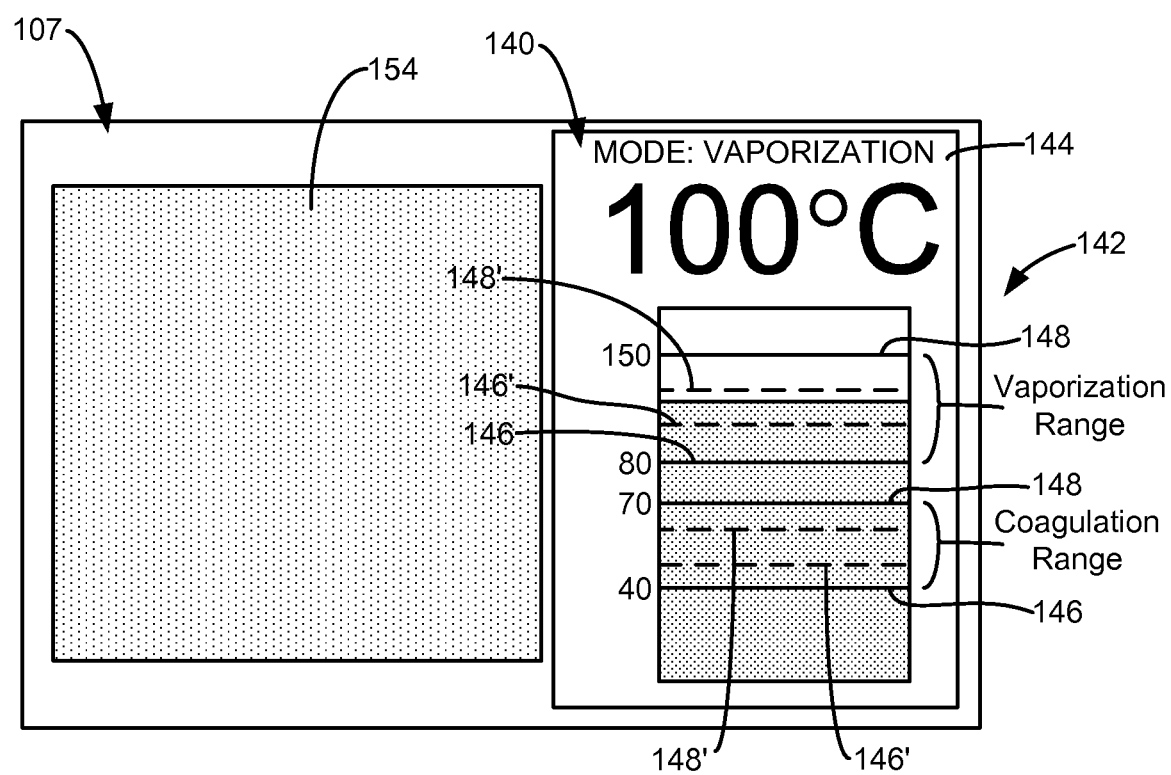
FIG. 8 is a simplified diagram of a display in accordance with embodiments of the invention.

As described above, the controller 108 is configured to produce an image 140 on the display 107 based on the output signal 112. In some embodiments, as depicted in FIG. 8, the image 140 includes temperature information and/or operating mode information 144, both of which are determined based on the approximate temperature indicated by the output signal 112. The temperature information indicates the approximate temperature at the treatment site 121. In some embodiments, the temperature information indicates an average approximate temperature at the treatment site, which is calculated using the controller 108 based on samples of the output signal 112 taken over a period of time, such as 0.1-1.0 seconds. In some embodiments, the operating mode information 144 indicates a laser treatment being performed at the treatment site 121 or on a targeted object 120 using the laser energy 110.

In some embodiments, the image 140 includes information regarding the Joule usage. Including the Joules currently being used at the treatment site 121 allows the physician to determine the efficiency of the laser treatment being performed. For example, if the physician knows that 100 KJ has been used and he/she knows there is high vaporization at the treatment site, he/she knows that vaporization is being performed efficiently. However, if 100 KJ has been used and he/she knows there is low vaporization occurring at the treatment site, this may be an indication of low vaporization efficiency, which could lead to overheating of the laser fiber 104 or the targeted tissue 120. This additional information will allow a physician to identify and control the efficiency of the laser treatment being performed at the treatment site as well as help prevent the laser fiber 104 from overheating.

The image 140 produced on the display 107 using the controller 108 changes in response to changes to the output signal 112. That is, as the output signal 112 indicates a change in the temperature information (i.e., approximate temperature at the treatment site 121) or the operating mode information, the image produced on the display 107 by the controller 108 changes. Preferably, these changes to the image 140 are produced in substantially real-time. As a result, as the output signal 112 indicates a change in the approximate temperature at the treatment site 121, the image 140 produced on the display 107 changes to indicate this change in the approximate temperature. Likewise, changes in the output signal 112 that indicate a change in the operating mode result in a change in the operating mode information 144 produced in the image 140. Based on these changes in temperature and/or operating mode, the physician can compensate in real-time as deemed necessary in order to continue with the laser procedure. For example, the physician can alter the way the procedure is being performed (i.e., the distance of the fiber tip from the targeted object 120 can be changed, etc.) or can change the operating inputs of the laser device, i.e., the physician can increase or decrease the power of the laser device, or the physician can change the laser pulse widths, repetition rate, modulation, wavelength, etc.

In some embodiments, the image 140 includes a graphical display of the temperature information, as shown in FIG. 8. For instance, the temperature information may be presented in the image 140 in the form of a bar graph 142. Lower approximate temperatures at the treatment site 121 are indicated by a shorter bar, and higher approximate temperatures at the treatment site 121 are indicated by a higher bar. In some exemplary embodiments, the graphical display indicating the temperature information may include a line chart that presents the approximate temperature at the treatment site or target object over time.

In some embodiments, the temperature information is presented alphanumerically in the image 140 on the display 107. For instance, the temperature information in the image 140 may include the approximate temperature (e.g., 100° C.) indicated by the current output signal 112.

In some embodiments, the temperature information in the image 140 is represented both graphically and alphanumerically, as shown in FIG. 8. Additionally, the bar graph 142 may include the current approximate temperature listed adjacent the bar graph, as well as a temperature scale for the bar graph.

In some embodiments, the system 100 is configured to operate in at least two different operating modes, each corresponding to a different laser treatment (i.e., vaporization and coagulation) or any others described above. In some embodiments, the system 100 determines the mode of operation and the laser treatment being performed by the laser energy 110 based on the output signal 112 using the controller 108.

In some embodiments, the laser treatments and operating modes that are identifiable by the system 100 each have a corresponding approximate temperature range that is bounded by upper and lower approximate temperatures. In some embodiments, the approximate temperature ranges of each of the modes of operation of the system 100 do not overlap. In some embodiments, the memory 132 of the system 100, or other memory, includes a mapping of the approximated temperature indicated by the output signal 112 and the corresponding operating mode or laser treatment, which is accessible by the controller 108.

During operation, the controller 108 determines the laser treatment being performed at the laser treatment site 121 by comparing the approximate temperature indicated by the output signal 112 to the approximate temperature ranges associated with each of the laser treatments or operating modes of the system 100, which, as mentioned above, may be stored in the memory 132. When the approximate temperature indicated by the output signal 112 falls within one of the approximate temperature ranges of the laser treatments being monitored by the system 100, that laser treatment is determined to be the laser treatment currently being performed at the laser treatment site 121. Operating mode information indicating the current operating mode or laser treatment can then be presented in real-time in the image 140 on the display 107 using the controller 108 allowing the physician to see the conditions at the treatment site 121 as they are occurring. For example, in FIG. 8, the operating mode 144 is vaporization. In some exemplary embodiments, the image indicating the operating mode or laser treatment being performed may include a line chart or other indicator that presents the period of time an operating mode or laser treatment (i.e., vaporization, coagulation, etc.) has been performed at the treatment site or on the target object.

In one exemplary embodiment, the controller 108 is configured to determine whether the system 100 is in a coagulation mode, in which the laser treatment being performed at the laser treatment site is a coagulation treatment, based on the output signal 112. The coagulation treatment causes blood exposed to the laser energy 110 at the laser treatment site to coagulate. In another exemplary embodiment, the controller 108 is configured to determine whether the system 100 is in a vaporization mode, in which the laser treatment being performed at the laser treatment site is a vaporization treatment, based on the output signal 112. The vaporization treatment vaporizes tissue, blood, or other targeted object 120 in response to exposure to the laser energy 110 at the laser treatment site. Other embodiments involve the identification of other operating modes of the system 100 and laser treatments by the controller 108 using the output signal 112. In a further exemplary embodiment, the controller 108 is configured to determine whether the system is in coagulation mode or vaporization mode as indicated by the operating mode 144 in FIG. 8.

In some embodiments, the coagulation mode of operation has an approximate temperature range of between approximately 40-70° C. In some embodiments, the vaporization mode of the system 100, in which a vaporization laser treatment is performed at the laser treatment site, has an approximate temperature range of between approximately 80-150° C.

In some embodiments, the controller 108 is configured to convert the output signal 112 from a time-based signal to a frequency-based signal. This may allow the system 100 to extract more information from the electromagnetic energy feedback 114. The signal conversion can be accomplished through a frequency analysis of the output signal 112 using a frequency analyzer, or through the application of a Fourier transform to the output signal 112.

In some embodiments, the frequency-based output signal 112 can be used to identify the laser treatment being performed at the laser treatment site 121. For instance, the controller 108 can determine whether the system 100 is operating in a coagulation mode or a vaporization mode based on the frequency-based output signal 112. In some embodiments, a coagulation treatment is indicated when the frequency-based output signal 112 comprises lower frequency components that are relatively stable because during coagulation, no bubbles or debris are being created at the treatment site 121. During a vaporization treatment, tissue debris and bubbles may form at the treatment site, which will disturb the laser energy feedback 114 collected from the fiber tip 116. This disturbance is manifested in the frequency-based output signal being less stable and having higher frequency components than that found in the frequency-based signal corresponding to a coagulation treatment. Thus, in some embodiments, the controller 108 can distinguish different modes of operation based on an analysis of the frequency-based output signal produced in response to the electromagnetic energy feedback 114.

In some embodiments, the operating mode information in the image 140 comprises alphanumeric and/or graphical information indicating the current operating mode of the system 100. In some embodiments, the alphanumeric information includes a listing of the current operating mode or laser treatment (e.g., vaporization), as indicated at 144 of the image 140.

In some embodiments, the graphical information in the image 140 indicating the current operating mode or laser treatment includes a lower approximate temperature boundary 146 and an upper approximate temperature boundary 148 for each operating mode, as shown in FIG. 8. In some embodiments, the temperature information, such as the bar graph 142, indicates the approximated temperature relative to the boundaries 146 and 148, as shown in FIG. 8.

In some embodiments, the operating mode information in the image 140 comprises a graphical display having a color that corresponds to the current operating mode. For instance, when the approximate temperature corresponding to the output signal 112 indicates that the laser treatment being performed at the laser treatment site 121 is a coagulation treatment, the operating mode information in the image 140 includes a graphical image having a color that corresponds to the coagulation mode. Likewise, when the output signal 112 indicates that a vaporization treatment is being performed at the treatment site 121, the controller 108 produces the image 140 having a graphical image of a color that corresponds to the vaporization mode of operation. As a result, the physician can quickly determine the laser treatment currently being performed based on a color being displayed in the image 140 on the display 107. This color may be presented, for example, as highlighting of the bar graph 142, the listing of the operating mode, the display of the approximated temperature, a background of the image 140, or in another suitable manner.

In some embodiments, each of the approximate temperature ranges of the laser treatment modes performed by the system 100 have a target approximate temperature range corresponding to the preferred approximate temperature for performing the laser treatment. For instance, coagulation laser treatments may be most efficient at a target approximate temperature range of between approximately 50-60° C., and vaporization laser treatments may be performed most efficiently within a target approximate temperature range of between approximately 100-120° C.

In some embodiments, the operating mode information produced in the image 140 indicates the target approximate temperature range for at least one of the operating modes. In some embodiments, the target approximate temperature range for a mode or laser treatment is presented graphically in the image 140 by a lower approximate temperature boundary 146' and an upper approximate temperature boundary 148' of the targeted approximate temperature range, as shown in FIG. 8.

In some embodiments, the operating mode information for each operating mode (i.e., coagulation or vaporization) includes at least two colors that may be produced in the image 140 to indicate the mode of operation. One of the colors for each mode of operation indicates that the approximate temperature indicated by the output signal 112 is within the approximate temperature range of the mode of operation, but is not within the target approximate temperature range for the mode of operation (i.e., outside of boundary lines 146' and 148' but within boundary lines 146 and 148). The second color is used to indicate that the approximate temperature indicated by the output signal 112 is within the target approximate temperature range for the mode of operation (i.e., between boundaries 146' and 148'). As mentioned above, the color may be presented, for example, as highlighting of the bar graph 142, the listing of the operating mode, the display of the approximated temperature, a background of the image 140, or in another suitable manner.

In some embodiments, the operating mode information in the image 140 changes based on the approximate temperature indicated by the output signal 112 and the proximity of the approximate temperature to one of the approximate temperature boundaries 146 or 148 of an operating mode. In operation, as the approximate temperature rises toward a lower approximate temperature boundary 146 of an operating mode, the operating mode information produced in the image 140 may indicate (alphanumerically and/or graphically in any manner previously disclosed) that the approximate temperature at the laser treatment site is not high enough to perform the laser treatment corresponding to the operating mode. As the approximate temperature rises to the lower approximate temperature boundary of the operating mode, the operating mode information produced in the image 140 indicates (alphanumerically and/or graphically in any manner previously disclosed) that the laser treatment is being performed. As the approximate temperature rises further into the target approximate temperature range for the operating mode, the operating mode information in the image 140 may indicate (alphanumerically and/or graphically in any manner previously disclosed) that the approximate temperature is within the target approximate temperature range for the operating mode. As the temperature rises and exceeds the upper boundary 148' of the target approximate temperature range, the operating mode information produced in the image 140 may indicate (alphanumerically and/or graphically in any manner previously disclosed) that the laser treatment associated with the operating mode is still being performed at the laser treatment site, but that the approximate temperature is no longer within the target approximate temperature range. When the approximate temperature exceeds the upper approximate temperature boundary 148 for the operating mode, the operating mode information produced in the image 140 indicates (alphanumerically and/or graphically in any manner previously disclosed) that the laser treatment is no longer being performed.

In some embodiments, the controller 108 determines the type of fiber 104 being used for a specific laser treatment being performed at the laser treatment site 121 by comparing laser fiber 104 information stored in the memory 132 with information from the current fiber 104 being used. The memory 132 can also include the operating parameters for each laser fiber 104 capable of being used with the system 100. Accordingly, the controller 108 can be configured to compare the stored, safe operating parameters for the laser fiber 104 being used with operating information for the laser fiber 104 during use in performing a laser treatment. If the operating information for the laser fiber 104 during use (i.e., fiber tip temperature) falls outside the acceptable operating parameters, the controller 108 can automatically shut down the system or take other action, such as reducing laser power, in order to prevent damage to the laser fiber 104.

In some embodiments, the laser fiber 104 may be supported within an endoscope 150, a distal end of which is illustrated in FIG. 2. In some embodiments the system 100 includes a viewing fiber 152, a distal end of which is illustrated in FIG. 2. The viewing fiber 152 may be used, for example, to capture images of the treatment site 121, or perform other functions.

In some embodiments, the controller 108 is configured to produce an image 154 received through the viewing fiber 152 on the display 107, as indicated in FIG. 8. In some embodiments, the image 154 from the viewing fiber and an image 140 produced by the controller 108 based on the output signal 112, may be simultaneously displayed on the display 107, as shown in FIG. 8. As mentioned above, the image 140, based on the output signal 112 may include temperature information and/or operating mode information.

In some embodiments, the system 100 includes an output device 160, as shown in FIG. 1. In some embodiments, the controller 108 is configured to output an audible signal using the output device (e.g., speaker) based on the output signal 112. In some embodiments, the audible signal includes temperature information indicative of an approximate temperature at the treatment site, and/or operating mode information indicating a laser treatment being performed at the treatment site. For instance, the audible signal may verbally indicate the approximate temperature and/or the operating mode. In some embodiments, the audible signal includes a tone that's indicative of the approximate temperature and/or operating mode. For instance, the audible signal may have a pitch, amplitude, or pattern indicating the temperature information or operating mode information. In some embodiments, the pitch, amplitude, or pattern of the audible signal changes in response to changes in the approximate temperature indicated by the output signal 112. In some embodiments, the audible signal may include a verbal indication, a pitch, amplitude, or pattern indicating which operating mode or laser treatment is being performed and/or whether such laser treatment is within any of the target approximate temperature ranges.

In some embodiments, the system includes an input device 162 that the physician may use to control the laser energy 110 discharged from the laser source 102. In some embodiments, the input device comprises a dial, a keypad, a touchscreen, or other suitable input device that allows the physician to adjust the power level of the laser energy 110 generated by the laser source 102. This adjustment to the power of the laser energy may involve controlling a power supply 164, controlling a shutter mechanism 165, modulating the laser energy 110, adjusting a duty cycle of the laser energy 110, adjusting the power of the input light to the laser gain medium of the laser resonator within the laser source 102, or other conventional adjustment that modifies the power of the laser energy 110 output from the laser source 102. In some embodiments, the input device 102 also allows the physician to adjust the laser pulse widths, repetition rate, modulation and/or wavelength.

Figure 9:
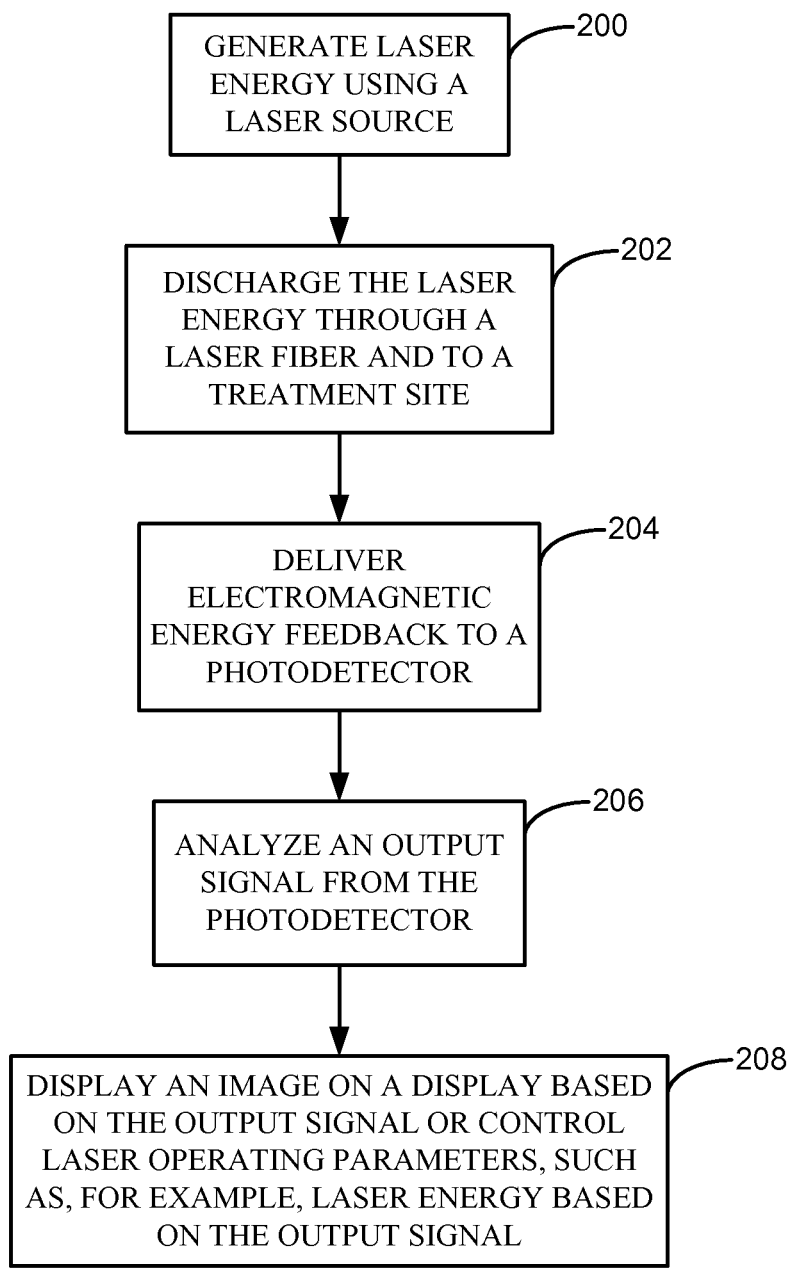
FIG. 9 is a flowchart illustrating a method of operating a surgical laser system in accordance with embodiments of the invention.

In some embodiments, the system 100 operates to maintain a desired approximate temperature or operating mode that the physician would like the system 100 to operate at. In some embodiments, the physician inputs the desired temperature or operating mode through the input device 162. In some embodiments, the controller 108 controls the laser source 102 to automatically adjust the laser energy 110 output from the laser source 102 based on the output signal 112 to maintain the approximate temperature at the laser treatment site 121 at or near the desired temperature set by the physician, to maintain the approximate temperature at the laser treatment site 121 within the range of approximate temperatures associated with the desired operating mode selected by the physician, or to maintain the laser treatment mode desired, i.e., vaporization or coagulation. The adjustment to the power of the laser energy 110 may be performed in accordance with any suitable technique, such as adjusting a duty cycle of the laser energy, adjusting a modulation of the laser energy, adjusting the intensity of the input light to the laser gain medium of the laser resonator of the laser source 102, or other technique. Additional adjustments that can be made include, and are not limited to, laser pulse widths, repetition rate, and/or wavelength FIG. 9 is a flowchart illustrating a method of operating a surgical laser system 100 in accordance with embodiments of the present invention. In general, the method involves using the surgical laser system 100 in accordance with one or more of the embodiments described herein, to perform a laser treatment at a treatment site 121 of a patient. Each of the steps may be performed using the controller 108 in response to the execution of program instructions stored in the memory 132 or other location, for example.

At 200 of the method, laser energy 110 is generated using a laser source 102. At 202, the laser energy 110 is discharged through a fiber 104 to the treatment site 121. At 204, electromagnetic energy feedback 114 is delivered to a photodetector 106. At 206, an output signal 112 generated by the photodetector 106 in response to the electromagnetic energy feedback 114 is analyzed. At 208, an image 140 is displayed on a display 107 based on the output signal 112 using the controller 108. Alternatively, at 208, the laser energy 110 generated by the laser source 102 can be automatically adjusted by the controller 108 based on the output signal 112 in order to maintain the desired laser treatment conditions parameters, i.e., vaporization, coagulation, temperature at the treatment site/target object, etc. Each of the method steps recited above may be performed using one or more of the embodiments of the surgical laser system 100 disclosed and described above.

In some embodiments of step 206, the output signal 112 from the photodetector 106 is analyzed in real-time using the controller 108. In some embodiments, the time-based output signal 112 is used to determine temperature information in the form of an approximate temperature at the treatment site 121. This may be accomplished by comparing an intensity of the electromagnetic energy feedback 114 to a look-up table, stored in the memory 132 or other location, that maps the intensity to a corresponding approximate temperature.

In some embodiments of step 206, the output signal 112 is used to determine operating mode information in the form of an operating mode of the system 100 or a laser treatment being performed at the treatment site 121. In some embodiments, the controller 108 compares an approximate temperature or intensity indicated by the output signal 112 to a look-up table, stored in the memory 132 or other location, that correlates the approximate temperature or intensity to a corresponding operating mode or laser treatment.

In some embodiments, the controller 108 or a suitable frequency analyzer is configured to perform a frequency analysis of the output signal 112 to produce a frequency-based output signal 112. In some embodiments, the frequency-based output signal 112 is used by the controller 108 to determine an operating mode of the system 100 or a laser treatment being performed at the treatment site 121, as described above.

In some embodiments of step 208, the image 140 produced by the controller 108 on the display 107 includes temperature information and/or operating mode information. In some embodiments, the temperature information indicates an approximate temperature at the treatment site 121 based on the output signal 112. In some embodiments, the temperature information includes an alphanumeric and/or graphical representation of the approximate temperature indicated by the output signal 112.

In some embodiments, the operating mode information presented in the image 140 indicates a mode of operation of the system 100, and/or laser treatment being performed at the treatment site 121. In some embodiments, the operating mode information is represented alphanumerically and/or graphically in the image 140.

Although the present invention has been described with reference to preferred embodiments, workers skilled in the art will recognize that changes may be made in form and detail without departing from the spirit and scope of the invention.

What is claimed is:

1. A surgical laser system comprising:
   a laser source configured to generate laser energy;
   a laser fiber optically coupled to the laser source and configured to discharge the laser energy and collect electromagnetic energy feedback from a treatment site;
   a photodetector configured to generate an output signal in response to the electromagnetic energy collected from the treatment site; and
   a controller configured to produce an image or indication about at least one condition at the treatment site on a display based on the output signal,
   wherein the controller is configured to convert the output signal from a time-based signal to a frequency-based signal, and
   wherein the controller is configured to identify one or more treatment modes using the frequency-based signal.

2. The surgical laser system of claim 1, wherein the output signal corresponds to the at least one condition at the treatment site.

3. The surgical laser system of claim 2, wherein the at least one condition at the treatment site includes temperature and/or the one or more treatment modes.

4. The surgical laser system of claim 3, wherein the one or more treatment modes includes vaporization and/or coagulation.

5. The surgical laser system of claim 1, wherein the image includes temperature information, which is based on the output signal, the temperature information indicating an approximate temperature at the treatment site where the laser energy is discharged by the laser fiber, or an average approximate temperature at the treatment site over a period of time.

6. The surgical laser system of claim 5, wherein the image includes a graphical display of the temperature information or an alphanumeric display of the temperature information.

7. The surgical laser system of claim 5, wherein the image indicates that the one or more treatment modes are not capable of being performed in response to the approximate temperature at the treatment site being outside a predetermined temperature range.

8. The surgical laser system of claim 1, wherein the image includes treatment mode information based on the output signal, the treatment mode information indicating a laser treatment being performed on the treatment site where the laser energy is discharged by the laser fiber.

9. The surgical laser system of claim 8, wherein the image includes treatment mode boundaries indicating upper and lower operating parameters of at least one of the one or more treatment modes.

10. The surgical laser system of claim 1, wherein the controller is configured to control the laser energy discharged through the laser fiber responsive to the output signal.

11. The surgical laser system of claim 1, further comprising an input device, wherein the controller is configured to control the laser energy discharged through the laser fiber responsive to a user input received from the input device.

12. The surgical laser system of claim 1, wherein a color of the image corresponds to a current treatment mode.

13. The surgical laser system of claim 1, wherein the controller is configured to:
   identify a vaporization mode when the frequency-based signal has a first stability; and
   identify a coagulation mode when the frequency-based signal has a second stability, wherein the second stability is lower than the first stability.

14. A method of operating a surgical laser system comprising the steps of:
   generating laser energy using a laser source;
   discharging the laser energy through a laser fiber to a treatment site;
   receiving electromagnetic energy feedback from the treatment site produced in response to discharging the laser energy to the treatment site at a photodetector;
   generating a photodetector output signal;
   analyzing the photodetector output signal using a controller;
   converting the output signal from a time-based signal to a frequency-based signal;
   displaying treatment site information on a display based on the photodetector output signal analyzed by the controller; and
   identifying one or more treatment modes using the frequency-based signal.

15. The method of claim 14, wherein displaying the treatment site information includes displaying temperature information based on the output signal, the temperature information indicative of a temperature at the treatment site.

16. The method of claim 14, wherein displaying the treatment site information includes displaying at least one of the one or more treatment modes of the surgical laser system.

* * * * *